(12) United States Patent
Joist

(10) Patent No.: US 7,344,513 B2
(45) Date of Patent: Mar. 18, 2008

(54) DEVICE FOR TREATING HUMAN AND/OR ANIMAL TISSUE

(76) Inventor: Alexander Joist, Wittenbergring 26, Lingen (DE) 49808

( * ) Notice: Subject to any disclaimer, the term of this patent is extended or adjusted under 35 U.S.C. 154(b) by 626 days.

(21) Appl. No.: 10/240,702

(22) PCT Filed: Mar. 20, 2001

(86) PCT No.: PCT/EP01/03168
§ 371 (c)(1),
(2), (4) Date: Apr. 28, 2003

(87) PCT Pub. No.: WO01/76491
PCT Pub. Date: Oct. 18, 2001

(65) Prior Publication Data
US 2003/0163136 A1    Aug. 28, 2003

(30) Foreign Application Priority Data
Apr. 5, 2000    (DE)    ............... 200 06 247 U

(51) Int. Cl.
*A61M 5/46* (2006.01)
*A61B 17/16* (2006.01)
(52) U.S. Cl. .......................................... 604/43; 606/80
(58) Field of Classification Search ............... 604/43; 606/162
See application file for complete search history.

(56) References Cited

U.S. PATENT DOCUMENTS

| 4,706,659 A | 11/1987 | Matthews et al. ............ 128/92 |
| 5,613,972 A * | 3/1997 | Lee et al. ..................... 606/107 |
| 5,624,393 A | 4/1997 | Diamond ..................... 604/48 |
| 5,694,951 A | 12/1997 | Bonitti et al. ............... 128/898 |
| 5,849,023 A | 12/1998 | Mericle ....................... 606/180 |
| 5,913,859 A | 6/1999 | Shapira ....................... 606/80 |
| 5,947,972 A | 9/1999 | Gage et al. .................... 606/80 |
| 6,332,886 B1 * | 12/2001 | Green et al. .................. 606/80 |

FOREIGN PATENT DOCUMENTS

| EP | 0 861 635 | 9/1998 |
| WO | WO 97/03611 | 2/1997 |

* cited by examiner

*Primary Examiner*—David H. Willse
(74) *Attorney, Agent, or Firm*—Ohlandt, Greeley, Ruggiero & Perle, L.L.P.

(57) ABSTRACT

A device for working human and/or animal tissue is provided. The device includes a drill head is connected with a flexible shaft which in turn is connected to a drill apparatus through a shank. The device also includes a washing unit through which drilled material in the area of the drill head is transported away. The washing unit is connected to a washing channel formed between the bore and the outer diameter of the flexible shaft. The drill head has slots communicating with an inner cavity of the drill head. The cavity communicates with an inner channel in the flexible shaft through which the washing medium is passed into a washing head. In the washing head, the washing medium flows through the slots in the flexible shaft into an annular groove. The annular groove is connected with a channel to which a suction device is connected via a hose.

7 Claims, 3 Drawing Sheets

DEVICE FOR TREATING HUMAN AND/OR ANIMAL TISSUE

FIELD OF THE INVENTION

The present invention refers to a device for working on human and/or animal tissue, in particular an arthroscope, an endoscope or a core drill, in particular a intramedullary reamer for long bones such as femurs.

DISCUSSION OF THE BACKGROUND ART

Arthroscopy is used to enter cavities in human or animal joints so as to work on the surface of a bone, for example. This work may be the smoothing of the surface. Further, arthroscopy is also useful in removing tissue, such as in the removal of bone parts from joints by milling, scraping and the like. In endoscopy, human tissue is treated in similar fashion; however, endoscopy is not employed in joint cavities but in any other part of the human or animal body.

With fractures of long tubular bones such as femurs, both bone parts are first aligned and then bored in the longitudinal direction. Subsequently, a nail is inserted into the bore to fix both bone parts.

The bore is provided by first inserting a guide pin into the bone marrow of both bone parts. The guide pin is a wire with a diameter of 2 to 3 mm. The guide pin serves to guide a drill head. The drill head is connected to a flexible shaft driven by a drill drive, such as a pneumatic drill.

When forming the bore, high pressure is generated at the drill head. This pressure pushes bone and fat tissue into venae. In this context, there is a chance of those particles being transported into the lung via the blood vessel and causing pulmonary embolism. In particular, if besides the bone fracture also the lungs are injured, the two bone parts cannot be fixed by the nailing describe above since the risk of pulmonary embolism would be too high. Thus, the bone can only be fixed from outside. As a consequence, the fracture often heals poorly, an proper anatomic setting of the fracture is difficult, infections of the soft-tissue environment occur frequently, and, possibly, the definite treatment of the fracture has to be performed in a second surgical operation.

CH 687 228 A5 discloses a special drill head for intermedullary reaming designed to reduce the pressure at the drill head. The drill head has openings through which the drilled material, primarily the bone marrow, can be transported rearward. However, since a flexible shaft is located in the drill hole, there is only little space for accommodating the drilled material. Thus, the amount of drilled material is larger than the space behind the drill so that the drilled material is further compressed. Thus, pressure builds up in the area of the drill head. This may result in drilled material being washed out into the lung via blood vessels and causing pulmonary embolism.

The problems of increased pressure build-up are also disadvantageous when endoscopes and arthroscopes are used and may cause the above mentioned problem, respectively.

SUMMARY OF THE INVENTION

It is the object of the invention to provide a device for working on human and/or animal tissue, in particular a core drill, especially useful for intermedullary reaming in tubular bones, which avoids pressure build-up at the working head.

When the device of the present invention is a core drill, it comprises a washing unit by which the drilled material is transported away from the area of the working head. In a core drill, the working head is a drill head. By continuously washing, the material removed, i.e., the drilled material, is washed out from the medullary space of the bone, for example, so that no pressure can be generated within the bone and especially at the drill head. Due to the pressure-less core drill according to the present invention, the risk of drilled material being washed into the lung and, thus, the risk of pulmonary embolism is avoided.

According to the invention, the core drill comprises a flexible shaft with an inner channel. Further, the drill head connected to the flexible shaft has openings in communication with the inner channel. According to the invention, a washing unit is provided, having a contact surface that allows the washing unit to be applied to an object in a substantially sealed manner. If the core drill is used for intermedullary reaming, the object is a tubular bone. Further, according to the invention, the diameter of the working head, as well as that of the drill head, is larger than the outer diameter of the flexible shaft so that a washing channel is formed between the outer surface of the flexible shaft and the drill hole produced in an object, such as a tubular bone.

When drilling tubular bones, a washing medium is introduced into the washing channel from the washing unit. Thus, the washing medium flows along the outer surface of the flexible shaft towards the drill head. Since the washing unit has a contact surface that substantially seals off the bone surface, the washing medium can be introduced into the washing channel in a simple manner. At the drill head, the washing medium flows into the interior of the drill through the openings in the drill head. In the process, the washing medium takes up the drilled material and transports the same inward through the openings in the drill head. Since the openings communicate with the inner channel of the flexible shaft, the washing medium is transported into the interior of the flexible shaft. In the inner channel of the flexible shaft, the washing medium and the drilled material are carried out from the bone towards the washing unit.

The washing medium may also be transported in reversed directions, so that the washing medium flows through the inner channel of the flexible shaft to the drill head, leaves from the openings thereof and is discharged from the bone through the washing channel. However, discharging the washing medium through the inner channel of the flexible shaft is advantageous in that the drilled material is not guided along the inner wall of the bore. This could cause the drill hole to become clogged and might thus lead to injuries at the inner wall of the bore.

Providing a washing unit is further advantageous in that no heat is generated at the drill head that could cause tissue changes.

Preferably, the washing unit comprises a suction device to generate a vacuum at the drill head. Generating the vacuum guarantees that all drilled material is discharged immediately. Thereby, the occurrence of pressure is avoided at the drill head, which could cause drilled material to enter the blood vessels of a patient. Preferably, the suction device is connected with the inner channel of the flexible shaft so that the washing medium is sucked out through the inner channel together with the drilled material. This is advantageous in that the sealing between the contact surface of the washing unit and the object need not be of a particularly well sealing design, since no high pressures occur at the contact surface in this direction of suction.

Preferably, the flexible shaft has a plurality of articulately connected shaft segments. By providing a plurality of shaft segments, a uniform torque can be transmitted. Compared to known flexible shafts of spirally wound wire, the flexible shaft of shaft segments has the advantage that no catching and a subsequent sudden free rotation of the drill head by the flexible shaft relaxing can occur. With flexible shafts of spirally wound wire, a corresponding torque can be built up by twisting the wire. When the drill head is suddenly released, the flexible shaft of twisted wire relaxes. Thereby, the torques transmitted become non-uniform.

Preferably, a hose is provided in the shaft having a plurality of shaft segments. The hose seals the inner channel of the flexible shaft off against the washing channel, since drilled material could otherwise get between the individual shaft segments and into the washing channel. Further, the drilled material could impair the flexibility of the shaft if drilled material accumulates between the individual shaft segments. With a reversed transport direction of the washing medium, i.e., if drilled material is discharged through the washing channel, the flexible shaft should be enclosed by a hose to avoid drilled material accumulations between the shaft segments.

The washing unit, which is applied on the outside of an object or a bone, preferably comprises a washing head. The flexible shaft is rotatably held in the washing head. The washing medium transported outward through the inner channel of the flexible shaft, enters the washing head from the inner channel and is discharged therethrough. To this end, the flexible shaft has openings in the area of the washing head, while the washing head has an annular groove so that despite the rotation of the flexible shaft, the washing medium and the drilled material can be discharged from the inner channel into the annular groove and from there outward.

Preferably, the washing head is displaceably supported in a guiding element of the washing unit. Thus, the contact surface of the washing unit can be held firmly on the object or the bone and simultaneously serves as a guide for the flexible shaft and the drill head. The flexible shaft is thus guided in the guiding element together with the drill head and the washing head so as to make the bore in the object or the bone.

The flexible shaft preferably comprises a plurality of shaft segments. Each shaft segment comprises at least one projection and a recess engaging a recess or a projection of an adjacent shaft segment so that projections and recesses interlock. The dimensions of the projections and recesses are adjusted to each other such that a gap is formed that extends around the shaft circumference. The interlocking projections and recesses of adjacent shaft segments are further designed such that they engage behind each other in the longitudinal direction. Thereby, the shaft segments are permanently connected in the longitudinal direction of the shaft. Due to the circumferential gap, a mutual play between the individual shaft segments is obtained.

Depending on the magnitude of the play and the length of the individual shaft segments, the shaft is more or less flexible. By rotating a shaft segment connected to the drive, the gap between the shaft segments is closed partly so that the opposing gap surfaces are partly in contact. Power is transmitted via these contact areas from one shaft segment to the next. In this manner, the flexible shaft transmits a torque. To transmit higher torques, the shape of the projections and recesses may be designed such that contact areas as large as possible are obtained when rotating the shaft.

The individual shaft segments are preferably inherently rigid. They are preferably made of hard plastic material or metal and, especially, of titanium. Since the projection of one shaft segment engages into the recess of an adjacent shaft segment, the projection engages behind the recess, as provided by the invention. Thus, the projection comprises a neck-shaped and a head-shaped part. Similarly, the recess comprises a neck-shaped and a head-shaped part. The shaft segments are thereby permanently connected in the longitudinal direction. The design of the projections and recesses of the present flexible shaft also serves to transmit traction and pressure forces. The areas of the gap surfaces in which the shaft segments contact each other when transmitting traction or pressure forces, may preferably be formed such that a transmission surface is formed to reduce the surface pressure.

Preferably, each shaft segment has at least two projections and two recesses on the shaft circumference. The surface for force transmission between two shaft segments is thus increased. Preferably, the projections are of the same size and are arranged regularly along the circumference of the shaft. Thus, it is guaranteed that the flexible shaft has approximately the same flexibility in every direction of bending. Preferably, the ratio between the gap width and the shaft diameter is between 1:100 and 1:10 for round shaft segments. This means the gap width is between 0.1 and 1 mm for a shaft diameter of 10 mm. The selection of the gap width can influence the maximum possible bending of the flexible shaft. In order to increase the reliability of the transmission of torques, as well as of forces, it is advantageous to provide gap widths as small as possible, i.e., a gap width of only 0.5 to 0.1 mm for a shaft diameter of 10 mm. To increase flexibility, not the gap width should be increased, but the number of shaft segments by shortening the length of the individual shaft segments.

In medical applications, the present core drill is suitable not only as an intermedullary reamer, but also for loosening and washing out angiosclerosis as well as for removing nephroliths, uretheroliths and gallstones. To this avail, a gripping or catching device may additionally be provided at the drill head. According to the invention, the broken stones are carried away by washing.

The above described core drill is not only suitable for medical purposes, but for core drilling in general, where pressure build-up at the drill head is to be avoided. This is the case, for example, when the material surrounding the drill hole could be damaged by the pressure generated upon drilling. The present drill is thus particularly suitable for drilling soft plastic and natural materials. Since no pressure is built up at the drill head in the present core drill, the drill is especially well suited for brittle materials since these could be damaged by the pressure. For example, hairline cracks could occur in the material.

The present core drill can be implemented both on a large scale and in micro and nano technology.

After completion of the bore, material can be introduced into the drilled object through the inner channel of the flexible shaft. Thus, the drilled hole can be filled with filling material immediately upon withdrawing the drill, e.g. to stiffen the object.

In a preferred embodiment of the present invention, the flexible shaft itself can serve as a nail for connecting two bone pieces. To this end, the flexible shaft is connected or adapted to be connected with a tensioning device for stiffening the shaft. The tensioning device closes the gaps between the individual shaft segments. Thus, the tensioning device pulls the individual shaft segments together. Since the gap is designed such that tangential forces can be transmitted between the shaft segments, pulling the shaft segments together forms a non-flexible tube. The same may be used directly as a nail in a bone. Pulling together the individual shaft segments may be done, for example, by means of a suitable cable control or by compressing the flexible shaft.

Preferably, the flexible shaft further comprises an anchoring device for anchoring the shaft in the bone. Such an anchoring device is preferably designed such that, when the flexible shaft is tensioned, anchoring wedges or the like flip outward and cause the flexible shafts now stiffened to form a nail, to be anchored in the bone. Of course, the anchoring can also be effected before or after stiffening the shaft. Further, it is also possible to separately introduce anchoring elements into the inner channel of the flexible shaft and to insert them through corresponding openings in the shaft so that an anchoring of the shaft in the bone is achieved thereby.

The blades of the drill head are preferably formed such that the drill head, as soon as it meets a harder sheath after drilling soft core material, is deflected back into the core material. Thus, it is avoided that the drill emerges laterally from the object to be drilled, such as the bone.

The present invention for working on human and/or animal tissue, exemplified above by the core drill, is as well suitable for use as an arthroscope or an endoscope. The present arthroscope or endoscope also comprises a flexible shaft with an inner channel. The flexible shaft is connected with a working head with which tissue can be removed by smoothing, milling, scraping or the like, for example. The working head has openings which communicate with the inner channel. Further, the present arthroscope or endoscope has a washing unit. Corresponding to the above described core drill, the diameter of the working head, i.e. the maximum outer dimensions of the working head, which does not have to be a rotating tool, has to be larger than the outer diameter of the flexible shaft. Thus, a washing channel is formed by the outer surface of the flexible shaft and a hole in the object, i.e. the human tissue, for passing a washing medium therethrough.

In the present arthroscope, an additional working channel could be provided. For example, optics could be introduced therethrough in order to watch the working process. Further, washing fluid can be supplied through the working channel which can then be sucked off through the working head and the washing channel between the flexible shaft and the inner wall of the drill hole.

An arthroscope or endoscope according to the invention may be designed in a preferred manner corresponding to the above described core drill.

BRIEF DESCRIPTION OF THE DRAWINGS

The following is a detailed description of the invention with reference to the accompanying drawings.

In the figures.

Figure 1:
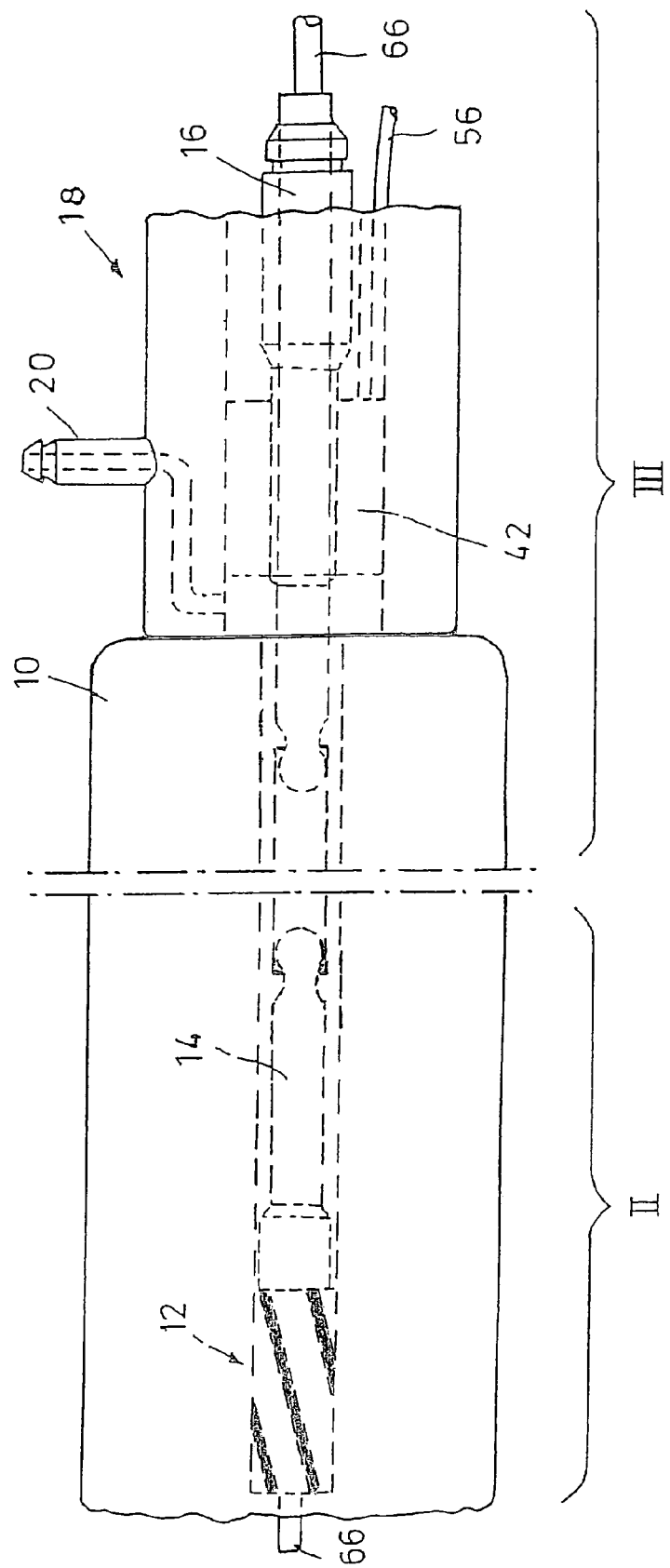
FIG. 1 is a schematic side elevational view of the core drill.

According to the invention, the core drill can be used in particular for core drilling in a tubular bone 10, such as a femur. For this purpose, the core drill comprises a drill head 12 connected to a flexible shaft 14. A shank 16 connects the flexible shaft 14 to the chuck of a drill, such as a pneumatic drill, for example. The core drill further comprises a washing unit 18 for transporting away the drilled material occurring in the area of the drill head 12, using a washing medium. In the medical field, the washing medium preferably is a saline solution. In other technical fields gases or other liquid medium can be used as the washing medium.

Figure 2:
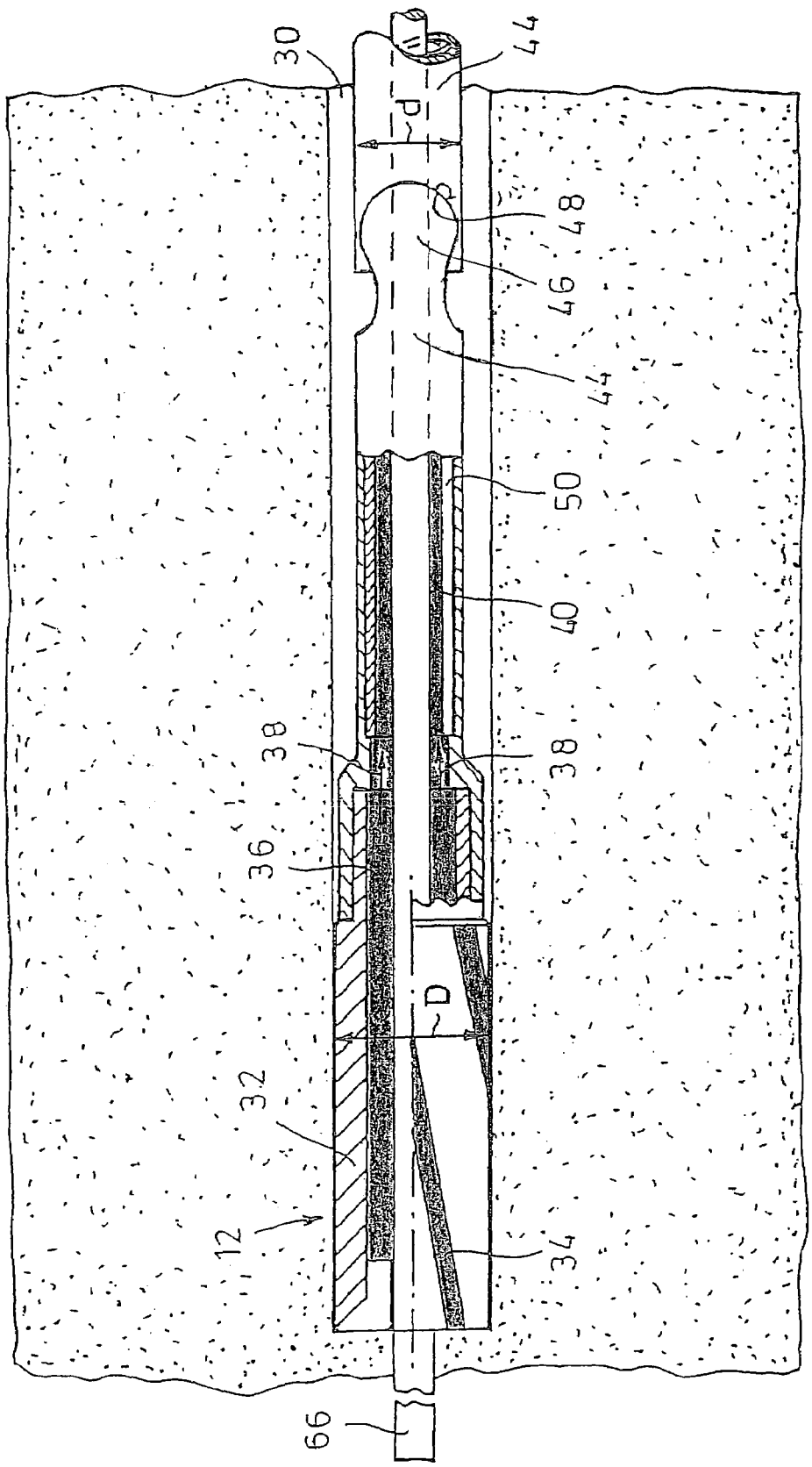
FIG. 2 is a schematic sectional view of the portion II in FIG. 1.
Figure 3:
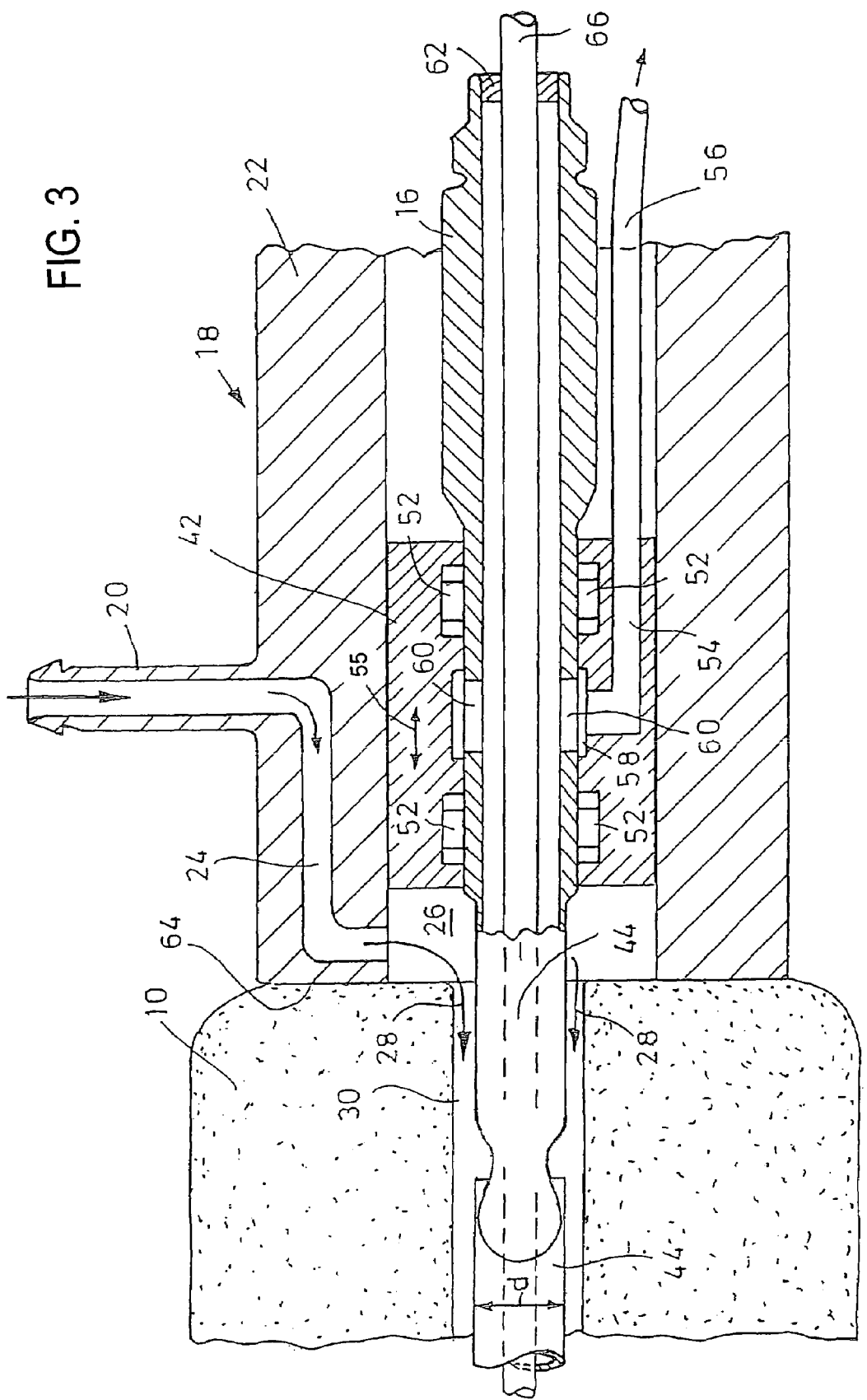
FIG. 3 is a schematic sectional view of the portion III in FIG. 1.

The washing unit 18 comprises an connection 20 connected by a hose to a reservoir containing washing medium. The washing medium is passed through a channel 24 provided in a guiding element 22 of the washing head 18. From the channel 24, the washing medium is supplied to a cylindric cavity 26 within the guiding element 22. From there, the washing medium flows into a washing channel 30 in the direction of the arrows 28. The washing channel 30 is provided between an outer diameter d of the flexible shaft 14 and the bore diameter D (FIG. 2). The bore diameter D corresponds to the drilling diameter D of the drill head 12. The washing medium reaches the drill head 12 through the washing channel 10 and is guided along blades 32 of the drill head 12. At the blades 32 of the drill head 12, the washing medium receives drilled material. When drilling tubular bones, this is primarily bone marrow. The bone marrow is carried away by the washing medium. To this end, the drill head has openings in the form of longitudinal slots 34 through which the washing medium can flow into the drill head 12.

The drill head 12 has a hollow interior so that the washing medium can flow through the slots 34 into the hollow interior 36 of the drill head 12. From the hollow interior 36 of the drill head 12, the washing medium flows in the direction of the arrows 38 into an inner channel 40 formed in the flexible shaft. The flexible shaft 14 is hollow along its entire length so that the inner channel 40 extends from the drill head 12 to the washing unit 18. The washing medium and the drilled material flow through the inner channel 40 to a washing head 42 provided in the washing unit 18.

The flexible shaft has a plurality of shaft segments 44. Each shaft segment has a plurality of projections 46 engaging into recesses 48 of the adjacent shaft segment 44. The projections 46 and the recesses 48 are designed such that the projections 46 and the recesses 48 engage behind each other in the longitudinal direction of the flexible shaft 14. Thus, the shaft segments 44 are permanently connected in the longitudinal direction. In order to guarantee the flexibility of the shaft 14, a gap is formed between the individual shaft segments 44 that extends along the entire circumference of the flexible shaft 14. The width of the gap and the length of the individual shaft segments 44 define the flexibility of the shaft 14. The projections 46, as well as the recesses 48, are preferably of the same size and are regularly arranged on the circumference of the flexible shaft 14. Thus, it is guaranteed that the flexibility of the shaft 14 is the same in any direction of deflection. Further, the gap has a constant width in the circumferential direction.

Since the washing medium could get into the washing channel 30 through the gaps between the shaft segments 44, whereby drilled material could get into the gaps and impair the flexibility of the shaft, the flexible shaft 14 is lined with a hose 50. The hose 50 extends from the drill head 12 to the shank 16.

The flexible shaft 14, via which the torque is transmitted from the drill to the drill head 12, is rotatably supported in the washing head 42 by bearings 52. Further, to be able to perform a drilling, the washing head 42 is supported for displacement within the guiding element 22 in the direction of the arrow 55, i.e. in the direction of drilling. Preferably, the washing head 42 is cylindrical so that it is displaceable in the cylindric cavity 26 of the guiding element 22. In order to avoid the washing head 42 from rotating along when drilling, the inner wall of the cylindric cavity 26 and the outer surface of the washing head 42 are provided with guiding elements. These may be grooves and corresponding projections. A seal is provided between the outer surface of the washing head 42 and the surface of the cylindric cavity 26 so as to prevent washing medium from escaping outward from the cylindric cavity 26 passing the washing head 42.

The washing medium transported from the drill head through the inner channel 40 in the flexible shaft towards the washing head 42 leaves the washing head 42 through a channel 54 and enters a hose 56 connected to a collecting vessel. For this purpose, the washing head has an annular groove 58. On the level of the annular groove 58, the flexible shaft 14 comprises a plurality of longitudinal slots 60 through which the washing medium flows from the inner channel 40 into the annular groove 58. The hose 56 is preferably connected with a suction device so that a vacuum is created at the drill head 12. This guarantees that no pressures occur in the area of the drill head when drilling the bone 10 which could cause drill medium to be transported, e.g. bone marrow being transported in venae. Thus, the risk of pulmonary embolism caused by drilled material being transported into the lungs is avoided.

The inner side, in particular at the end facing the drill head 12, the flexible shaft can have projections that cause the washing medium to rotate. For example, these are blade-like projections. Further, a kind of Archimedean screw may be provided. The inner side of the hose 56 may also be provided with a helical groove or a helical projection. Such elements cause the washing medium to rotate and the transport of the drilled material is improved.

In the upper portion of the shank 16, the inner channel 40 of the flexible shaft 14 is sealed by a seal 62 from the drill apparatus.

On the side facing the bone 10, the guiding element 22 of the washing unit has a contact surface 64 abutting the bone 10. By the contact surface, the washing unit 18 is sealed from the bone 10 so that no or only little washing medium can escape outward from the cylindric cavity 26 along the contact surface 64 and into the tissue surrounding the bone 10. In addition, washing medium is prevented from escaping along the contact surface 64 by providing a suction device at the hose 56 so that no increased pressures occur in the area of the cavity 26.

In order to avoid the drill head 12 of the core drill to penetrate the outer wall of the bone from the intermedullary space of the bone 10 outward, the blades of the drill head 12 are designed such that upon hitting the bone wall, i.e. harder material, from inside, the drill head 12 is deflected back into the intermedullary space. Thus, perforating the bone, i.e. a lateral escape of the drill head from the bone, is avoided.

This may also be achieved by providing a guide wire 66. The guide wire 66 extends through the shank 16, the hollow flexible shaft 14 and the drill head 12.

To effect a core drilling using a guide wire 66, the guide wire of a diameter between about 2 to 3 mm is first inserted through the bone. During the subsequent drilling of the bone 10, the drill head 12 is automatically guided by the guide wire 66 so that the drill head 12 cannot escape laterally from the bone 10. To make the bore in the bone 10, the guide wire 66 is thus introduced first. Then, the contact surface 64 of the washing unit 18 is set onto the bone. Thereafter, the washing head 42 is introduced into the cylindric cavity 26 of the guiding element 22 so that the drill head 12 contacts the bone 10 on the level of the contact surface 64. Then, the drill head 12 is rotated by the drill apparatus and moved in the direction of the arrow 55 together with the flexible shaft 14 and the washing head 42.

The washing unit 18 may be designed such that it does not serve as a guide for the washing head 42. In this embodiment, the cavity 26 is not sealed from the washing head 42 but from the outer surface of the flexible shaft 14. This is advantageous in that the guiding element 22 does not have to have the entire length of the bore.

The invention claimed is:

1. A device for working human and/or animal tissue comprising:
   a flexible shaft with an inner channel,
   a working head connected with the flexible shaft and having openings communicating with the inner channel, and
   a washing unit with a contact surface for a substantially sealed application on object,
   the diameter of the working head being greater than the outer diameter of the flexible shaft so that a washing channel is formed by the outer surface of the flexible shaft and a bore made in the object, the washing channel serving to pass a washing medium therethrough, wherein the flexible shaft has a plurality of articulately connected shaft segments and a hose is provided in the flexible shaft.

2. A device for working human and/or animal tissue comprising:
   a flexible shaft with an inner channel,
   a working head connected with the flexible shaft and having openings communicating with the inner channel, and
   a washing unit with a contact surface for a substantially sealed application on an object,
   the diameter of the working head being greater than the outer diameter of the flexible shaft so that a washing channel is formed by the outer surface of the flexible shaft and a bore made in the object, the washing channel serving to pass a washing medium therethrough, wherein the washing unit comprises a washing head in which the flexible shaft is rotatably supported.

3. The device of claim 2, wherein the washing head is supported for displacement in a guiding element of the washing unit.

4. A device for working human and/or animal tissue comprising:
   a flexible shaft with an inner channel,
   a working head connected with the flexible shaft and having openings communicating with the inner channel, and
   a washing unit with a contact surface for a substantially sealed application on an object,
   the diameter of the working head being greater than the outer diameter of the flexible shaft so that a washing channel is formed by the outer surface of the flexible shaft and a bore made in the object, the washing channel serving to pass a washing medium therethrough, wherein the flexible shaft has a plurality of shaft segments with mutually engaging projections and recesses which engage behind each other in the longitudinal direction, leaving a gap around the shaft circumference, so that the shaft segments are permanently connected in the longitudinal direction having mutual play.

5. The device of claim 3, wherein all projections are of the same size and are distributed regularly over the circumference of the shaft.

6. The device of claim 3, wherein the gap has a constant width in the circumferential direction.

7. The device of claim 3, wherein the ratio of gap width and shaft diameter is between 1:100 and 1:10.

* * * * *